(12) United States Patent
Knox

(10) Patent No.: US 10,016,308 B2
(45) Date of Patent: Jul. 10, 2018

(54) ABSORBENT MENSTRUAL CUP

(71) Applicant: Chante' Knox, Alpharetta, GA (US)

(72) Inventor: Chante' Knox, Alpharetta, GA (US)

(*) Notice: Subject to any disclaimer, the term of this patent is extended or adjusted under 35 U.S.C. 154(b) by 491 days.

(21) Appl. No.: 14/669,614

(22) Filed: Mar. 26, 2015

(65) Prior Publication Data
US 2016/0278988 A1    Sep. 29, 2016

(51) Int. Cl.
  *A61F 13/15*   (2006.01)
  *A61F 13/00*   (2006.01)
  *A61F 15/00*   (2006.01)

(52) U.S. Cl.
  CPC ...... *A61F 13/00085* (2013.01); *A61F 15/005* (2013.01)

(58) Field of Classification Search
  CPC .. A61F 13/0085; A61F 13/005; A61F 15/005; A61F 13/00085
  See application file for complete search history.

(56) References Cited

U.S. PATENT DOCUMENTS

| | | | |
|---|---|---|---|
| 3,128,767 A | | 4/1964 | Nolan |
| 3,216,422 A | * | 11/1965 | Steiger ............... A61F 5/4553 128/837 |
| 3,626,942 A | * | 12/1971 | Waldron ............... A61F 6/08 604/330 |
| 4,961,436 A | | 10/1990 | Koch |
| 5,295,984 A | | 3/1994 | Contente |
| 5,743,893 A | | 4/1998 | Kalb |
| 5,771,900 A | | 6/1998 | Austin |
| 5,947,992 A | * | 9/1999 | Zadini ............. A61B 17/12099 604/904 |
| 6,126,616 A | | 10/2000 | Sanyal |
| 6,168,609 B1 | | 1/2001 | Kamen |
| 6,264,638 B1 | * | 7/2001 | Contente ............. A61K 9/0036 128/832 |
| 6,796,973 B1 | | 9/2004 | Contente |
| 7,045,029 B2 | | 5/2006 | DeLucia |
| 8,454,493 B2 | | 6/2013 | La Vean |
| 2006/0069359 A1 | | 3/2006 | DiPalma |
| 2008/0200888 A1 | | 8/2008 | Gooch |
| 2010/0312204 A1 | | 12/2010 | Sheu |

\* cited by examiner

*Primary Examiner* — Jacqueline Stephens
(74) *Attorney, Agent, or Firm* — Larson & Larson, P.A.; Justin P. Miller; Patrick A. Reid

(57) ABSTRACT

The absorbent menstrual cup solves the problem of spillage while removing a menstrual cup by combining a flexible menstrual cup with a non-removable absorbent layer.

16 Claims, 4 Drawing Sheets

ABSORBENT MENSTRUAL CUP

FIELD

The described device relates to feminine hygiene products, specifically to those that collect vaginal menstrual discharge.

BACKGROUND

Devices for the absorption of menstrual discharge are known in the art, all seeking to solve the issue of discretely collecting menstrual blood. But the known devices each present significant drawbacks. Sanitary napkins are bulky and prone to leakage. Tampons are a less-bulky alternative. Tampons avoid the bulk of sanitary napkins through the use of an insertable and highly-absorbent material. By virtue of being in direct contact with the inner surfaces of the vaginal canal, the tampon readily absorbs all the fluids of the vagina.

Toxic shock syndrome is believed to be caused by the toxins produced by the bacterium *Staphylococcus Aureus*. Studies suggest that toxic shock syndrome is related to tampon absorbency, specifically that the higher the tampon absorbency, the higher the risk of incidence. Direct contact between tampons and the interior of the vaginal canal upsets the natural moisture balance of the vaginal canal by absorption of all natural fluids, in severe cases resulting in toxic shock syndrome.

What is needed is a device that provides for the sanitary disposal of menstrual fluids without the drawbacks of the prior art.

SUMMARY

The absorbent menstrual cup solves the problem of spillage while removing a menstrual cup by combining a flexible menstrual cup with a non-removable absorbent layer.

Furthermore, the absorbent menstrual cup solves the problem of prior art feminine products that absorb both menstrual fluids and beneficial vaginal fluids though contact between the absorbent material and the delicate vaginal mucosa. The absorbent menstrual cup solves this problem by separating the absorbent material from the wall of the vagina.

The absorbent menstrual cup is a flexible rim combined with a multi-layered reservoir. The flexible rim comfortably fits underneath the user's cervix, while the multi-layered reservoir gathers and contains the menstrual fluid. Unlike a contraceptive diaphragm, the absorbent menstrual cup does not require individual sizing to fit each user's cervix.

The flexible rim has an inner surface and outer surface. The inner surface may include inner grooves to help aid the flow of menstrual fluids. Such inner surface grooves or markings may facilitate the downward flow of the collected fluids. The outer surface may include outer projections to help the user grip the absorbent menstrual cup during insertion and removal.

The multi-layered reservoir is comprised of at least three layers. The outer reservoir layer is impervious to liquids. This both prevents menstrual fluid from seeping out of the absorbent menstrual cup and vaginal fluids from being absorbed into the device.

The one or more middle reservoir layers are absorbent, gathering the menstrual fluid and containing it.

The inner reservoir layer allows menstrual fluid to pass through to the middle reservoir layer. The inner reservoir layer is a fine mesh, nonstick material, or a perforated sheet comprised of a non-absorbent material. The inner reservoir layer acts to prevent contact between the absorbent layers of the absorbent menstrual cup and the user's tissue, while also providing a dry surface in case of contact between the user's hands and the reservoir during removal.

As a result of separating the absorbent layers from the vaginal walls, the absorbent menstrual cup is safe to wear for at least 8 hrs and up to 12 hrs.

The middle and inner layers may be affixed to the outer layer through the use of adhesive, fusing the layers together by melting, or mechanically coupling the layers together by clamping the rim over the layer edges.

The result is a single-piece, unified menstrual fluid reservoir. The intention is that the absorbent menstrual cup be a single-use device, being disposed of after a single use. Making the entire device disposable avoids the problems of requiring the user to handle contaminated absorbent layers, which results in unclean hands and an unclean reservoir that must be refilled with absorbent medium.

The flexible rim must be of sufficient thickness and resilience to maintain the shape of the absorbent menstrual discharge device. The layers that result in the reservoir are flexible and collapsible. As a result, the absorbent menstrual discharge device is readily inserted and removed, while remaining comfortable during use.

The absorbent menstrual cup is optionally constructed of entirely biodegradable materials.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
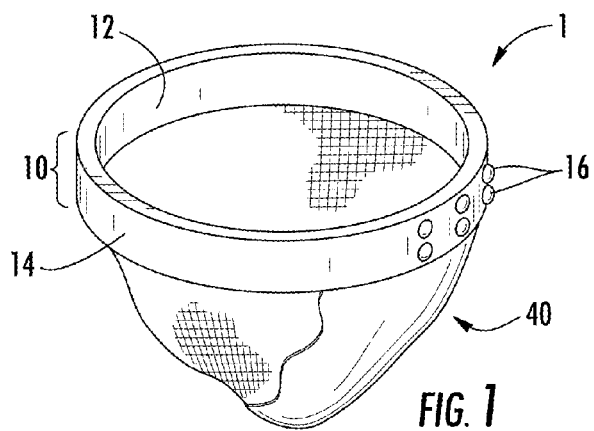
FIG. 1 illustrates an overall view of a first embodiment of the absorbent menstrual discharge device.

Reference will now be made in detail to the presently preferred embodiments of the invention, examples of which are illustrated in the accompanying drawings. Throughout the following detailed description, the same reference numerals refer to the same elements in all figures.

Referring to FIG. 1, an overall view of a first embodiment of the absorbent menstrual cup 1 is shown. The rim 10 is the section of the absorbent menstrual cup 1 that directly contacts the cervix. Rim 10 is comprised of rim inner surface 12 and rim outer surface 14. Rim inner surface 12 has optional rim outer projections 16, and rim outer surface 14 has optional rim inner grooves 18. Reservoir 40 is shown connected to the rim 10.

Figure 2:
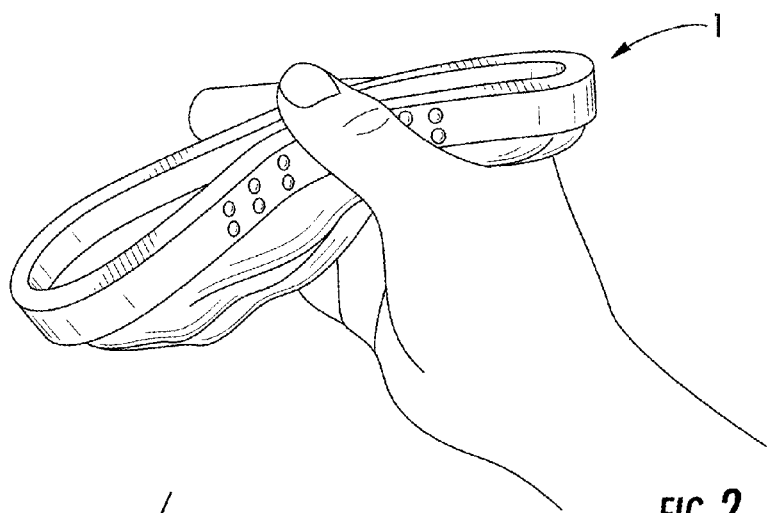
FIG. 2 illustrates a second view of the absorbent menstrual discharge device, showing how it can collapse for insertion and removal.

Referring to FIG. 2, a second view of the absorbent menstrual cup 1 is shown. The flexibility of the absorbent menstrual cup 1 is shown, an important feature for insertion and removal.

Figure 3:
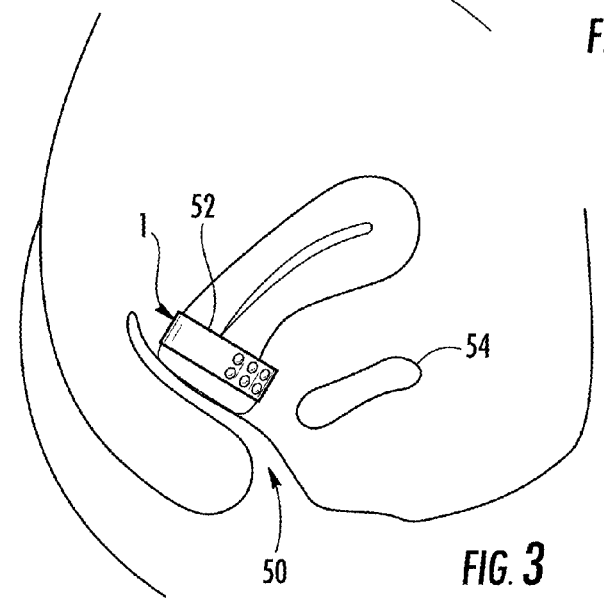
FIG. 3 illustrates a cross-sectional view of the absorbent menstrual cup after insertion and placement.

Referring to FIG. 3, a cross-sectional view of the absorbent menstrual cup 1 is shown. The absorbent menstrual cup 1 is inserted through the vaginal canal 50 and rests directly underneath the cervix 52 positioned behind the pubic bone 52.

Figure 4:
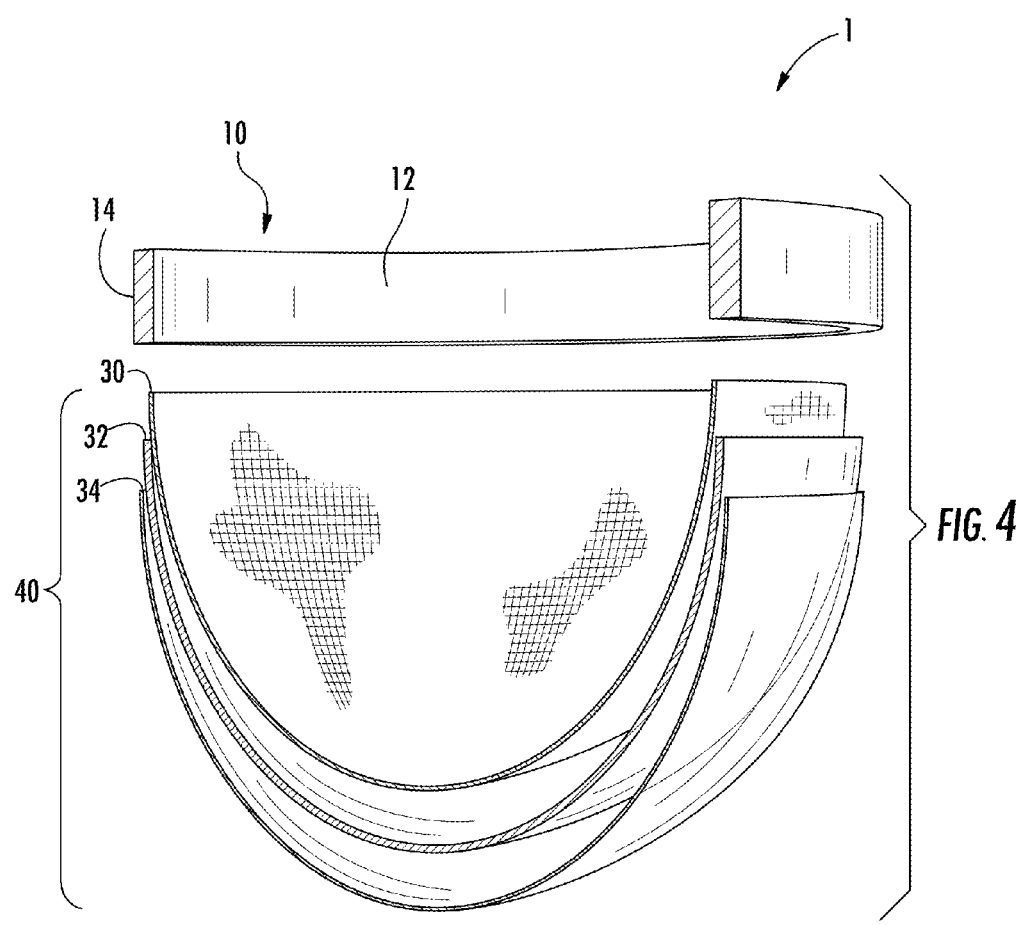
FIG. 4 illustrates an exploded view of the absorbent menstrual discharge device, showing the individual layers.

Referring to FIG. 4, an exploded view of the absorbent menstrual cup is shown. The reservoir 40 comprises three or more layers: the inner reservoir layer 30, which is a non-absorbent material such as plastic adapted to allow the passage of vaginal secretions and exfoliated cells and tissues; the middle reservoir layer 32, which is an absorbent material, such as cotton; and the outer reservoir layer 34, which does not allow liquids, such as menstrual fluid, to either leak away from the one or more absorbent layers, or to be drawn inward from the vaginal canal 50 into the one or more absorbent layers.

The absorbent menstrual cup 1 may include additional shapes or features that aid in removal. The features described below are designed to help the user remove the absorbent menstrual cup 1 from her body. Thus, it is important to remember that during use the absorbent menstrual cup 1 may be wet or slippery. Without a mechanism for the user to grip it may be difficult to remove.

Figure 5:
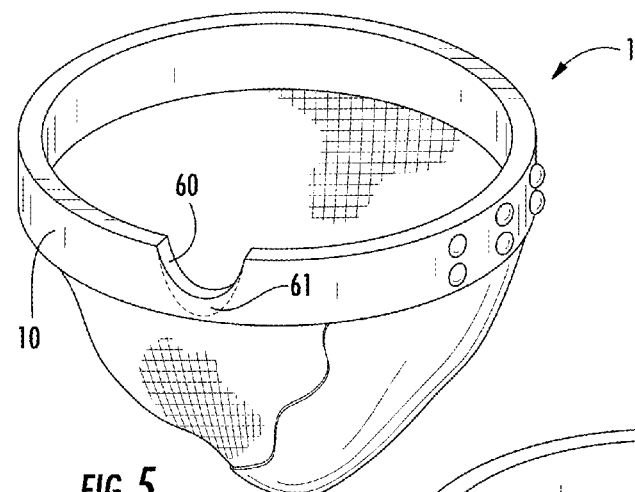
FIG. 5 illustrates an embodiment with a depression to aid removal.

Referring to FIG. 5, an embodiment with a depression 60 to aid removal is shown. Depression 60 is shaped and sized to fit a single finger. Internal inset 61 is thinner location of the rim 10, helping to keep the fingertip fixed in place. The user can insert her finger into depression 60, break the seal against the cervix, if any, and then pull downward to remove the absorbent menstrual cup 1.

Figure 6:
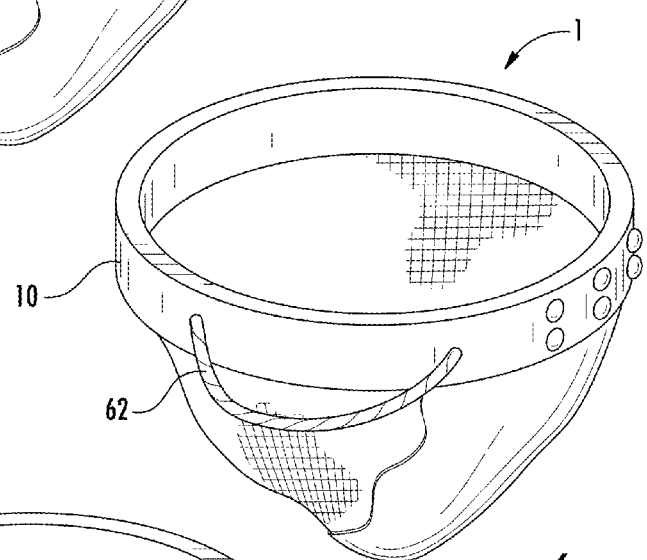
FIG. 6 illustrates an embodiment with a flexible loop to aid removal.

Referring to FIG. 6, an embodiment with a flexible loop 62 to aid removal is shown. Flexible loop 62 is a material different than that of the rim 10. For example, string, cord, twine, or rope. A flexible material is beneficial because it will not press against the user's vaginal canal 50, which may cause discomfort.

Figure 7:
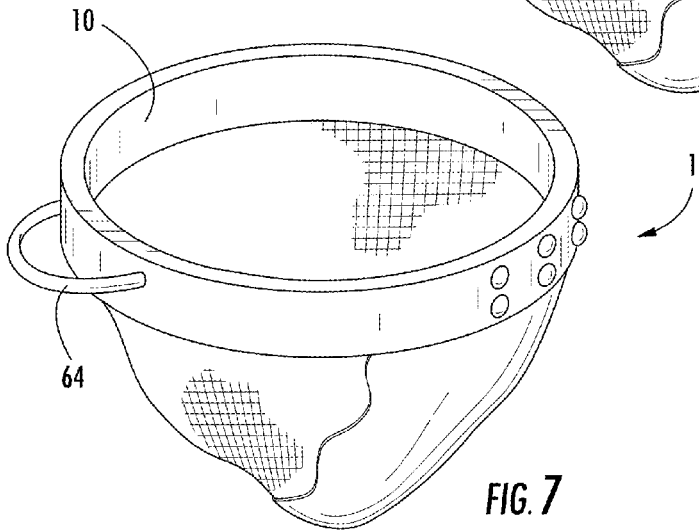
FIG. 7 illustrates an embodiment with a molded loop to aid removal.

Referring to FIG. 7, an embodiment with a molded loop 64 to aid removal is shown. The molded loop 64 can be the same material as the rim 10, or a second material. The molded loop 64 is anticipated to be a stiffer material than flexible loop 62. This stiffer material makes molded loop 64 easier for the user to locate within the vaginal canal 50 because its location is predicable. Flexible materials may move or become tucked into locations the user does not anticipate.

Figure 8:
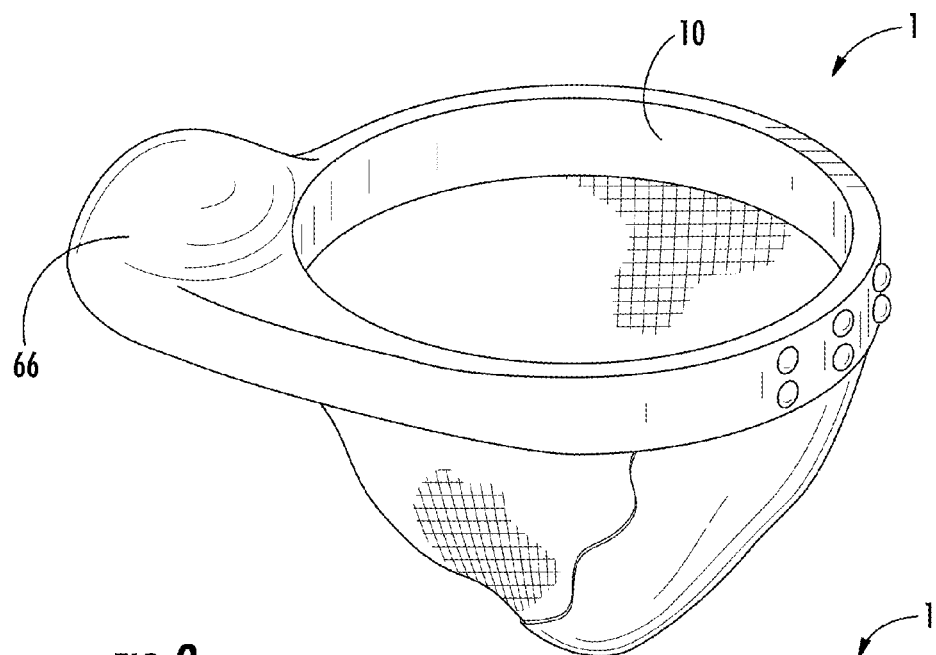
FIG. 8 illustrates an embodiment with a molded dome to aid removal.

Referring to FIG. 8, an embodiment with a molded dome 66 to aid removal is shown. Molded dome 66 is an extension of the rim 10. In order to remove the absorbent menstrual cup 1, the user hooks a finger under the dome 66 and pulls the absorbent menstrual cup 1 out of the vaginal canal 50.

Figure 9:
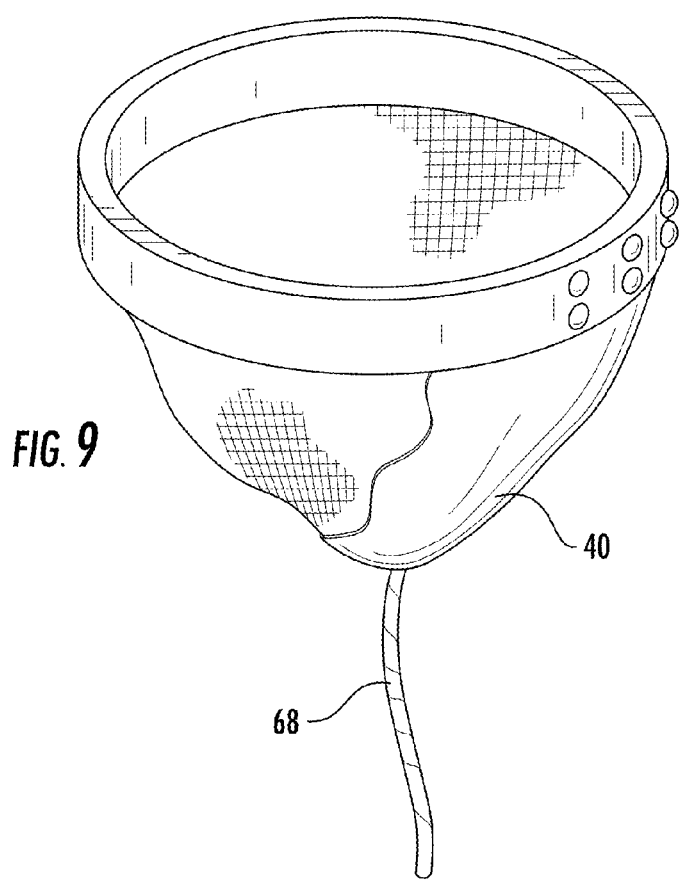
FIG. 9 illustrates an embodiment with a hanging string to aid removal.

Referring to FIG. 9, an embodiment with a hanging string 68 to aid removal is shown. The hanging string 68 is affixed to the base of reservoir 40. The hanging string 68 may be of any length, including long enough to protrude from the vaginal canal 50 while the absorbent menstrual cup 1 is in use. This simplifies removal, allowing the user to tug on the string 68 to pull out the absorbent menstrual cup 1.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A menstrual fluid collection device comprising:
 a. a flexible rim, said flexible rim having an inner surface and an outer surface; and
 b. a reservoir of three or more layers attached to the flexible rim including an inner layer of a porous material, at least one middle layer of an absorbent material, and an outer layer of a non-absorbent material;
  i. the inner layer bonded to the middle layer;
  ii. the middle layer bonded to the outer layer;
 c. whereby the layers form a single-piece structure without gaps.

2. The menstrual fluid collection device of claim 1, wherein the inner surface has one or more projections.

3. The menstrual fluid collection device of claim 1, wherein the outer surface has one or more grooves.

4. The menstrual fluid collection device of claim 1, wherein the inner layer of porous material acts to wick fluid through itself into the absorbent material.

5. The menstrual fluid collection device of claim 1, wherein the three or more layers cannot be readily separated.

6. The menstrual fluid collection device of claim 5, wherein three or more layers are thermally bonded.

7. The menstrual fluid collection device of claim 1, wherein the inner layer and middle layer cannot be removed from the menstrual fluid collection device.

8. The menstrual fluid collection device of claim 1, wherein during use a separation exists between the inner layer and an internal surface of a vaginal canal.

9. A menstrual fluid collection device comprising:
 a. a rim having an inner surface and an outer surface, said rim being made of a flexible material; and
 b. a unified reservoir comprised of an inner layer, a middle layer, and an outer layer;
 c. the inner layer, middle layer, and outer layer constructed without gaps between any two layers.

10. The menstrual fluid collection device of claim 9 wherein:
 a. said inner layer is made of a non-absorbent material adapted to allow vaginal secretions, exfoliated cells, and tissue to pass into the middle layer;
 b. said middle layer is made of an absorbent material such as cotton, or a material substantially similar to cotton; and
 c. said outer layer is made of a non-absorbent material that prevents leakage of absorbed vaginal secretions.

11. The menstrual fluid collection device of claim 9 wherein the inner surface of the rim includes projections.

12. The menstrual fluid collection device of claim 9, wherein the outer surface of the rim includes grooves.

13. The menstrual fluid collection device of claim 9, wherein three or more layers are thermally bonded.

14. The menstrual fluid collection device of claim 9, further comprising a depression in the rim, the depression sized to fit a finger.

15. The menstrual fluid collection device of claim 9, wherein during use a separation exists between the inner layer and an internal surface of a vaginal canal.

16. The menstrual fluid collection device of claim 9, further comprising a loop affixed to the rim, the loop designed to aid removal.

* * * * *